United States Patent [19]

Matsutani et al.

[11] Patent Number: 5,476,480
[45] Date of Patent: Dec. 19, 1995

[54] SURGICAL NEEDLE AND APPARATUS FOR GRINDING THE SAME

[75] Inventors: Kanji Matsutani; Hiroshi Yagisawa; Akira Saitoh, all of Tochigi, Japan

[73] Assignee: Kabushiki Kaisha Matsutani Seisakusho, Tochigi, Japan

[21] Appl. No.: 196,441

[22] Filed: Feb. 15, 1994

[30] Foreign Application Priority Data

Apr. 15, 1993 [JP] Japan .................................. 5-111155

[51] Int. Cl.6 ................................................. A61B 17/04
[52] U.S. Cl. ......................................... 606/222; 606/223
[58] Field of Search .................................. 606/222–227; 66/116, 117; D3/28

[56] References Cited

U.S. PATENT DOCUMENTS 5,002,564  3/1991  McGregor ................................. 606/223
5,030,228  7/1991  Wong et al. .............................. 606/222
5,342,397  8/1994  Guido ....................................... 606/224

Primary Examiner—Gary Jackson
Attorney, Agent, or Firm—Townsend & Banta

[57] ABSTRACT

A surgical needle for sutural treatment having a triangle or polygon body in cross section, including a blunt needle point with a plate or round end and at least two cutting edges to prevent a health care provider from mistakenly hurting themselves even if the needle comes into contact with the tissue of the health care provide, and to provide a property that enables the needle to pass smoothly through tissues. A first face of the body may be ground by a grinding apparatus specially made for the surgical needle to form a tapered slope and the cutting edges. By pressing a material piece of the needle in a V-shaped groove it forms a second and third face and readily produces a high quality surgical needle.

9 Claims, 5 Drawing Sheets

SURGICAL NEEDLE AND APPARATUS FOR GRINDING THE SAME

CROSS-REFERENCE TO RELATED APPLICATION

This application claims priority benefits under 35 U.S.C §119 of Japanese application Serial No. 5-111,155, filed Apr. 15th, 1993, the entire disclosure of which is incorporated herein by reference.

BACKGROUND OF THE INVENTION

1. Field of the Invention

This invention relates to a surgical needle for a suture and, more particularly, to a surgical needle having a triangular cross section at its body and a grinding apparatus for manufacturing the surgical needle.

2. Description of Related Art

Conventional surgical needles are known in the art, such as disclosed in Japanese Utility Model Publication, No. Showa-62-23,457 and Japanese Patent Publication, No. Heisei-1-54,075. Any of these surgical needles have a triangular cross section and a pointed body to reduce resistance against penetration when passed through the tissues.

Problems of infections among health providers and patients involved in infectious diseases, such as hepatitis, AIDS, MRSA (Methicillin-Resistant Staphylococcus Aureus), and whatever, are raised as major social problems these days. Such infections may happen by way of a fluid, such as blood or the like, and as a carrier when a health provider, such as a doctor or the like, inadvertently hurts herself or himself with medical instrument. Hence, a needle with a sharp point may hurt a health provider therefore, the health provider must pay close attention to handling needles due to the tremendous risks of infection resulting in the health provider enduring enormous mental pressure associated with risks.

SUMMARY OF THE INVENTION

It is an object of the present invention to provide a safe surgical needle which minimized the injury to a health provider even if the provider handles it in an improper manner and thereby to solve the problems happening in association with medical circumstances these days.

The foregoing object is accomplished with a surgical needle having a triangular cross section at a body to include a face tapered along a longitudinal direction of the body, and a pair of cutting edges provided at opposite ends of the face in a transverse direction of the body. An edge provided in opposition to the face is blunted so that the needle point never enters into tissues unless a predetermined force or above is applied thereto, thereby blunting a needle point to prevent a health provider from being hurt at mistake. After pushed into tissues by a certain force, the surgical needle passes through the tissues with the cutting edges incising the tissues under reduced resistance against penetration of the needle.

According to a preferred embodiment of the present invention, the cutting edges are formed separately from the needle point. The tapered face could be ground in a transverse direction perpendicular to the longitudinal direction to make the cutting edges sharper.

In another aspect of the present invention, the body of a surgical needle has a polygonal cross section. The surgical needle includes a first face tapered along a longitudinal direction of the body so that the body has thinner thickness on a tip side thereof, a pair of cutting edges provided at opposite ends of the first face in a transverse direction of the body, and a second face provided in opposition to the first face. The needle point of the surgical needle is formed in a plate shape so as to be blunt by the first and second faces. The blunt needle point gives increased resistance when pushed into tissues, thereby reducing the risks of hurting health providers by mistake.

In addition, an apparatus for grinding a face of a surgical needle tapered along a longitudinal direction of a body of the surgical needle which is able to manufacture the surgical needle having a polygonal cross section at the body. The apparatus includes a grinder for grinding in a transverse direction perpendicular to the longitudinal direction, and a workpiece table for holding a plurality of surgical needles. The workpiece table includes a top face defining a shape of a ground face of the surgical needle, and a plurality of grooves for holding a bottom side of each of the surgical needles, formed on the top face.

BRIEF DESCRIPTION OF THE DRAWINGS

The above and other objects and features of the present invention are apparent to those skilled in the art from the following preferred embodiments thereof when considered in conjunction with the accompanied drawings, in which.

DETAILED DESCRIPTION OF THE PREFERRED EMBODIMENTS

Figure 1:
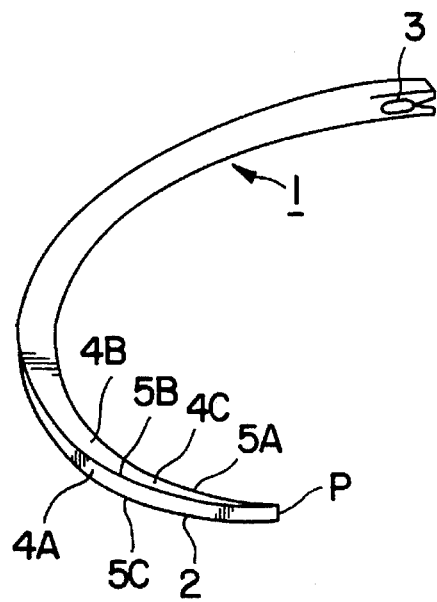
FIG. 1 is a perspective view showing a surgical needle according to a preferred embodiment of the present invention.
Figure 2:
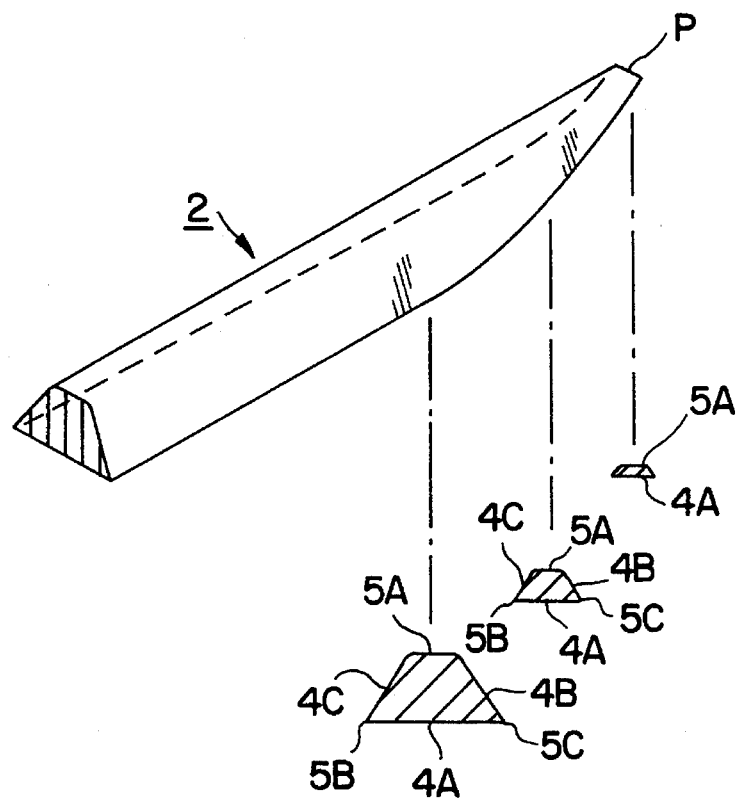
FIG. 2 is a perspective view showing a cutout of the body of the surgical needle in FIG. 1.

Referring to the drawings in detail, in particular, to FIGS. 1 and 2, surgical needle designated by numeral 1 according to a preferred embodiment of the invention is shown.

As shown in FIG. 1, the surgical needle 1 is a curved needle for sutural treatments having a triangular cross section. A body 2 is arranged on a tip side of the surgical needle 1, and an eye 3 is located on a shaft side for holding a suture. The body 2 has three faces 4A, 4B, and 4C, and three edges 5A, 5B, and 5C at which the three faces meet.

Among the faces, a first face 4A is an outer face of the curvature of the surgical needle 1, and is ground in a transverse direction by a polishing disk or the like. The other second and third faces 4B and 4C are made by a press within a mold therefor. A first edge 5A, among the three edges, is situated inside the curvature of the surgical needle and has a blunt verge. Second and third edges located on opposite sides of the first face 4A have sharp verges.

The body 2 has a configuration having a cross section as shown in FIG. 2 in succession up to a needle point P of the body. The first edge 5A has a dull, flattened ridge and reaches the needle point P while keeping the flattened top. To the contrary, the first face 4A is a successive surface that approaches to the first edge 5A as it gets closer to the needle point P, and makes the needle point P to be in a shape like a spatula.

On the other hand, although the second and third edges 5B, 5C are in succession up to the needle point P of the body 2, these edges 5B, 5C never meet at the needle point P to make the needle point to be blunt. That is, when the surgical needle 1 is put onto tissues, such as skin, the needle point P of the body 2 always contacts to the tissues through a liner or areal section, so that the surgical needle penetrates the surface of the tissues only when applied with a predetermined force or more. Once the needle 1 enters the tissues, sharp cutting edges 5B, 5C incise the tissues to reduce resistance against penetration, thereby allowing the health providers to handle the surgical needle 1 smoothly.

Figure 3A:
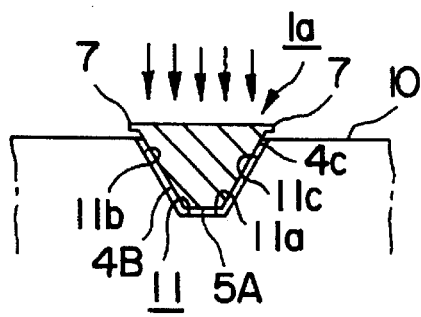
FIGS. 3(*a*) to 3(*c*) are fragmentary illustrations showing a manufacturing process of a surgical needle in FIG. 1.
Figure 3B:
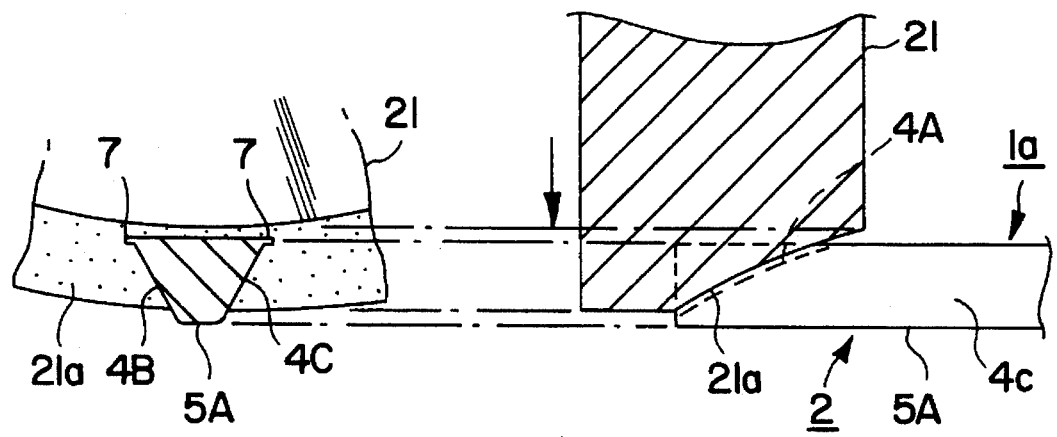
Figure 3C:
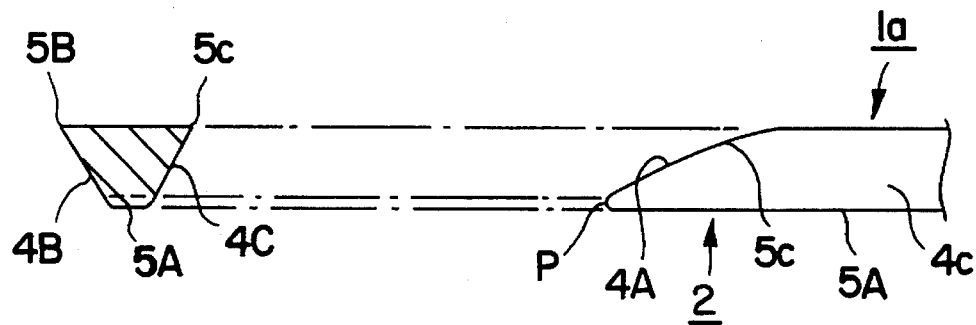
Figure 4A:
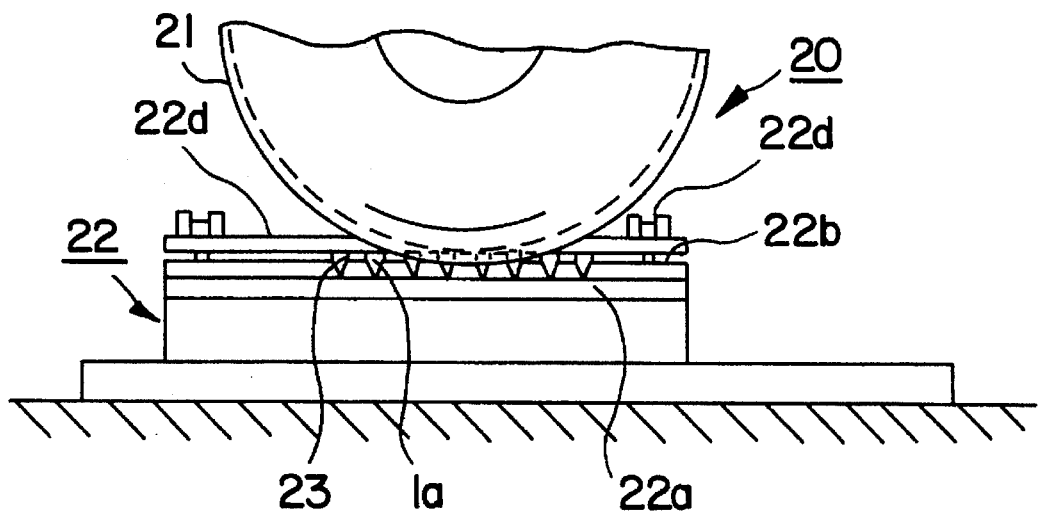
FIGS. 4(*a*), 4(*b*) are fragmentary illustrations showing operation of a grinding apparatus for grinding the surgical needle in FIG. 1.

Referring to FIGS. 3 and 4, a manufacturing process of the body 2 will be described. The curved needle as described in this embodiment is furnished to this shape by bending after the needle body is formed from a straight shaped material piece.

First, a material piece 1a made of stainless steel or the like is fixed to a mold 10 having a V-shaped groove 11 and pressed from the top side, as shown in FIG. 3(a). The material piece 1a, initially in a cylindrical shape, is transformed into a triangular prism by means of the V-shaped groove 11 through this work. The V-shaped groove is composed of a bottom face 11a and the groove side walls 11b, 11c by which the second and third faces 4B, 4C, pressed faces of the needle, are made. The bottom face 11a of the V-shaped groove 11 crushes the first edge 1A formed between the second and third faces 4B, 4C to be blunted. When pressed from its top side, the material piece 1a provides protruded portions, or burrs 7, 7, protruded from the pressed surface at top opposite ends in case the inserted material 1a has a large volume.

As shown in FIG. 3(b), a ground face 4A is formed at a portion opposite to the first edge 5A by grinding. This grinding work is conducted with the a grinding apparatus shown in FIG. 4. The grinding apparatus 20 includes a grinding disk 21 in which a rotary side face is used as a grinding face 21a, and a workpiece table 22 for setting a plurality of material pieces 1a through clamping. The grinding face 21a of the grind disk 21 contours a side face in the form of part of an ellipse as shown in FIG. 3(b).

Figure 4B:
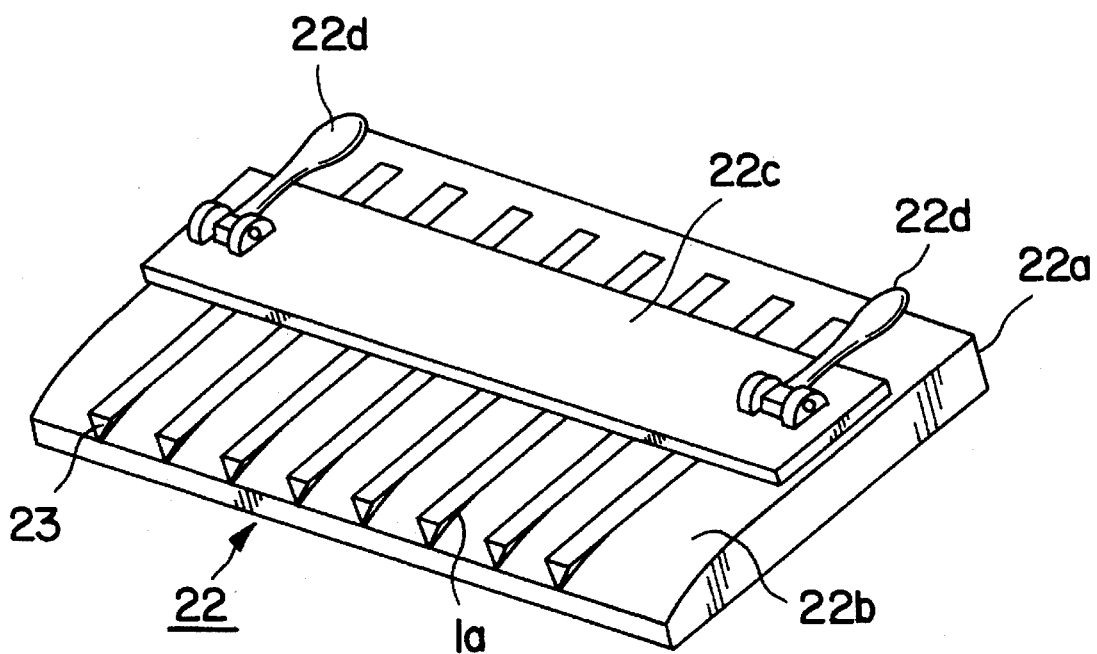

In FIG. 4(b), a perspective view of the workpiece table 22, a plurality of the V-shaped grooves 23 juxtaposed to one another are drilled on the top face 22b of the workpiece table body 22a. The triangular prism material pieces 1a machined at the process shown in FIG. 3(a) are set into the grooves 23. These material pieces 1a are fixed by being suspended between the fixing plate 22 and the workpiece table body 22a.

The top face 22b of the workpiece table body 22a has a gentle slope so as to coincide with the grinding side face 21b of the grind disk 21. Therefore, even where the grind disk 21 works for grinding, the grinding face 21a never interferes with the top face 22a of the workpiece table 22. In addition, since the material piece 1a is held by the V-shaped groove at the bottom side thereof, the material piece 1a is free from stress during grinding work, so that a high-quality surgical needle is produced.

The grinding face 21a of the rotating grind disk 21 contacts with the tip of the material piece 1a in such a manner, thereby forming the first face 4A on the material piece 1a as a ground face. FIG. 3(b) depicts a situation during grinding work. The ground face having a gently curved side shape is formed on and across the material 1a, and, as this grinding work goes on, the burrs 7, 7 are ground away, thereby forming sharp edges. This grind work is done by the grind disk 21 moving back and forth a number of times. Consequently, the grind disk 21 always grinds in the transverse direction perpendicular to the longitudinal direction of the material piece 1a, so that the first face 4A becomes a ground face with edges transversely oriented, thereby forming edges having excellent cutting property.

When the grind work ends, there produces the material piece 1a having the body 2 as shown in FIG. 3(c) is produced. That is, the first edge 5A having the flatten ridge and the ground first face 4A come close with one another at the needle point P of the body 2 to form a plate shape. The adjustment of the down feed amount of the grind disk allows thickness of the end of the needle point P to be set in various ways and, as a matter of course, allows the end of the needle point P to be formed into a liner shape. The second and third edges 5B, 5C are formed on the opposite sides, of the first face 4A, at which shaped edges are formed. On the other hand, such transverse grinding does not work against the edge at the needle point P because it is done in the extending direction of the edge, thereby producing the needle point P which is not easy to incise.

After this process, the material piece 1a is made to a surgical needle 1, as shown in FIG. 1, through a drilling process of an eye 3, not shown and a bending process. The surgical needle 1 according to this embodiment easily obtains the configuration feature described above only by being pressed and ground, thereby providing high productivity.

It is to be noted that although in the manufacturing process of the surgical needle according to the present invention the material piece 1a is transformed to the triangular prism by press in FIG. 3(a), the material piece could be pressed into a triangular pyramid using another mold after being ground in a cone and then be furnished to a body having a suitable triangular cross section during a grinding process done afterward. Although the surgical needle 1 is constituted so that the first face 5A is arranged inside of the curvature, the first face could be arranged outside of the curvature. Moreover, although the surgical needle 1 has the eye 3, as a construction for threading a suture, opened at a side face of the shaft of the needle, the surgical needle could be an eyeless needle with a long hole drilled to be open in the longitudinal direction of the body from the end of the shaft. In addition, although the needle has the curvature in this embodiment, the needle could be straight or hook shaped.

Referring to FIGS. 5 and 6, other shapes of the surgical needle according to the present invention are shown. FIG. 5 shows perspective views of various body types of the needle according to the present invention. FIG. 6 shows vertical cross-sections of various types of molds used for pressing.

Figure 5A:
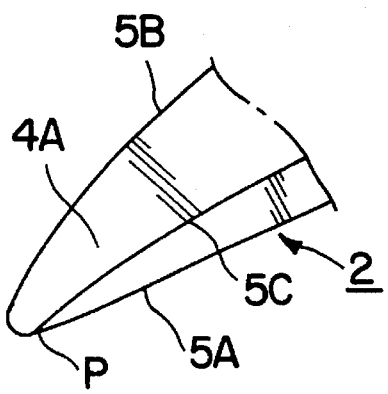
FIGS. 5(*a*) to 5(*f*) are perspective views showing point shapes of surgical needles according to other embodiments of the invention.
Figure 5B:
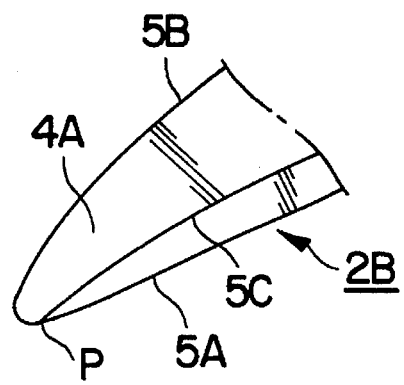
Figure 5C:
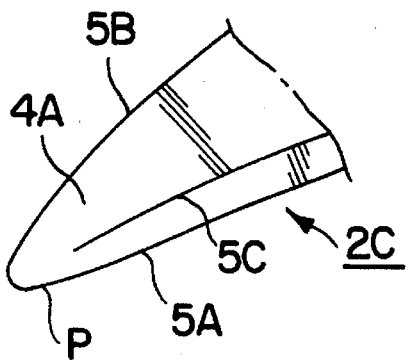
Figure 5D:
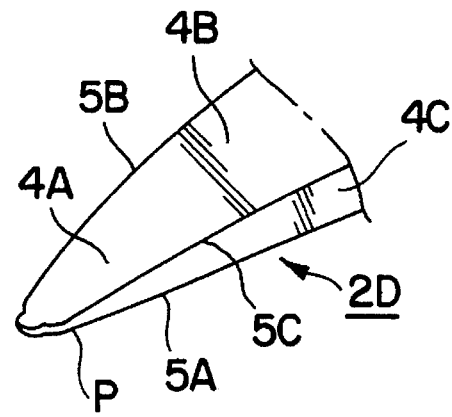
Figure 5E:
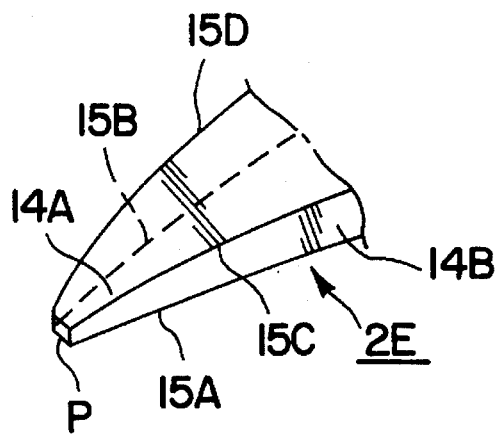
Figure 5F:
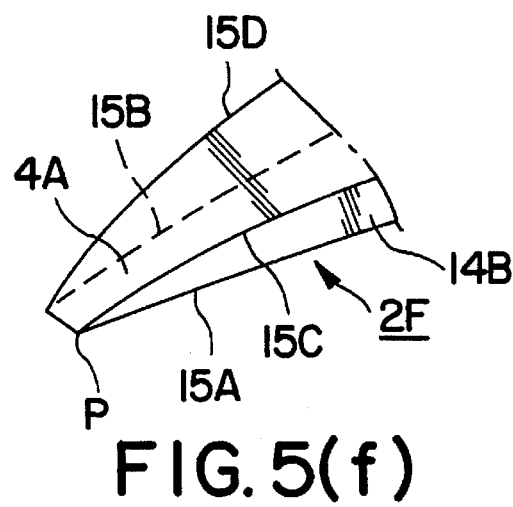

In FIG. 5(a), the body 2 has a knife shaped, ellipse, and round point. The top of the first edge 5A is crushed to be flatten, so that the point is in a plate shape as a result of grinding. A body 2B shown in FIG. 5(b) has a sharper ridge of the first edge 5A, and according to the sharper ridge point P becomes sharper. A body 2C shown in FIG. 5(c) is sharpened more than the body 2 or 2B by grinding. In this body 2C, second and third edges 5B, 5C are formed separately from the needle point P, so that the point P is round and blunt. A body 2D, as shown in FIG. 5(d), the second and third faces 4B, 4C are concave and respectively have an indentation along the longitudinal direction. A body 2E, as shown in FIG. 2E, has a rectangular cross section, different from the bodies 2, 2B, to 2D having triangular cross sections. This body 2E has four edges 15A to 15D, however, it is enough that the third and forth edges 15C, 15D have sharp ridges. The first face 14A and the second face 14B in opposition to the first face approach each other as they come close to the point P, and the point P becomes a plate shape. It is to be noted that although the body 2E has an areal end at the point P, the end could be a liner shape of a body 2F as indicated in FIG. 5(f) by adjusting the amount grinding amount.

Figure 6A:
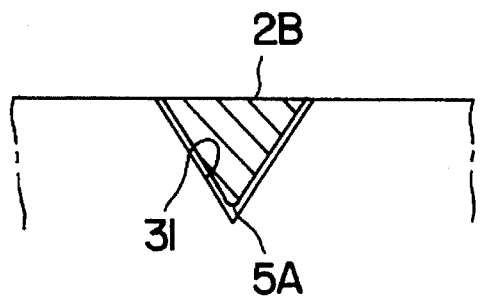
FIGS. 6(*a*) to 6(*c*) are cross-sectional diagrams illustrating molds used for pressing the surgical needles according to the invention.
Figure 6B:
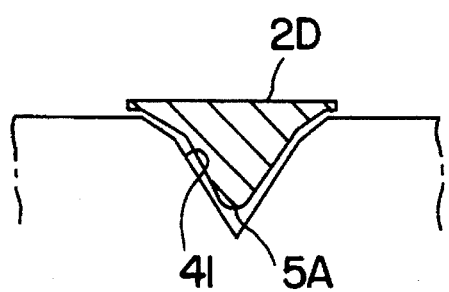
Figure 6C:
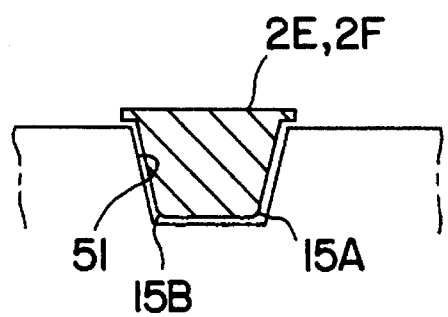

Such various types bodies 2, 2B to 2F are readily formed by changing molds used for press. FIGS. 6(a) to 6(c) show examples of mold shapes. The body 2B shown in FIG. 5(b) can be formed with a mold in FIG. 6(a). This mold has no bottom face in the V-shaped groove 31 which is different from the mold of the embodiment described above and shown in FIG. 2(a), and therefore, a material piece 1a pressed by this mold has a sharper first edge 5A. However, though the V-shaped groove 31 has a tapered lower end, the tapered end is not transferred to the material 1a because of the nature of the press, and the first edge 5A remains blunt. Adjustment of capacity of the mold can prevent the material piece 1a from being pressed with burrs at the partition line of the mold as shown in FIG. 6(a).

The body 2D in FIG. 5(d) is pressed by a mold 41 shown in FIG. 6(b). Using such a mold 41 allows the concave second and third faces 5B, 5C to be readily formed. The bodies 2E, 2F in FIGS. 5(e), 5(f) can be produced using a groove 51 having a rectangular cross section as shown in FIG. 6(c).

Resistance against entering of the surgical needle i into tissues is determined by a contact area with the tissues at a time that the point P is put up on the tissues. Changing the shape of the point to various ones allows the resistance to be adjusted. That is, it is enough that the point P has at least a shape by which pressure on the needle is dispersed, and since the skin is elastic, the end of the body might be a liner or areal shape as long as an incising point of the skin does not occur.

Thus, diversifying press formation of the material piece 1a using various types of molds allows various needle points to be produced without changing other processes, for example, the grinding process. Accordingly, this manufacturing process makes it possible to produce a safe point of the surgical needle according to this invention with various shapes mainly with the purpose that it will be used as a the surgical needle.

It is understood that although the present invention has been described in detail with respect to preferred embodiments thereof, various other embodiments and variations are possible to those skilled in the art which fall within the scope and spirit of the invention, and such other embodiments and variations are intended to be covered by the following claims.

What is claimed is:

1. A surgical needle having a triangular cross section at a body thereof, said surgical needle comprising:
   a face tapered along a longitudinal direction of said body so that said body has thinner thickness on a tip side thereof than on the opposite side;
   a pair of cutting edges provided at opposite sides of said face in a longitudinal direction of said body; and
   a blunt edge provided in opposition to said face, said blunt edge expanding to a needle point so that said surgical needle has no sharp point.

2. A surgical needle as set forth in claim 1, wherein at said needle point said cutting edges are spaced a part.

3. A surgical needle as set forth in claim 1, wherein said face is ground in a transverse direction perpendicular to said longitudinal direction.

4. A surgical needle as set forth in claim 1, wherein said body has curvature.

5. A surgical needle as set forth in claim 1, wherein said body is straight.

6. A surgical needle as set forth in claim 1, wherein said face is formed by grinding and other faces of the surgical needle are formed by press.

7. A surgical needle as set forth in claim 1, wherein said needle point has a contact area for contacting tissues, said contact area providing a predetermined resistance against entry of said needle into said tissue.

8. A surgical needle as set forth in claim 2, wherein said face is ground in a transverse direction perpendicular to said longitudinal direction.

9. A surgical needle having a polygonal cross section at a body thereof, said surgical needle comprising:
   a first face tapered along a longitudinal direction of said body so that said body has thinner thickness on a tip side thereof than on the opposite side;
   a pair of cutting edges provided at opposite sides of said first face in a longitudinal direction of said body;
   a second face provided in opposition to said first face; and
   a needle point formed in a plate shape by and between said first and second faces.

* * * * *